(12) United States Patent
Young et al.

(10) Patent No.: US 9,770,290 B2
(45) Date of Patent: *Sep. 26, 2017

(54) ABLATION PROBE WITH FLARED ELECTRODES

(71) Applicant: Boston Scientific Scimed Inc., Maple Grove, MN (US)

(72) Inventors: Kimbolt Young, Newtonville, MA (US); Jeffrey W. Zerfas, Bloomington, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 261 days.

This patent is subject to a terminal disclaimer.

(21) Appl. No.: 14/321,162

(22) Filed: Jul. 1, 2014

(65) Prior Publication Data

US 2014/0336639 A1    Nov. 13, 2014

Related U.S. Application Data

(63) Continuation of application No. 12/418,456, filed on Apr. 3, 2009, now Pat. No. 8,951,250, which is a continuation of application No. 10/977,274, filed on Oct. 28, 2004, now Pat. No. 7,524,318.

(51) Int. Cl.
*A61B 18/14* (2006.01)

(52) U.S. Cl.
CPC ........ *A61B 18/148* (2013.01); *A61B 18/1477* (2013.01); *A61B 2018/143* (2013.01); *A61B 2018/1425* (2013.01); *A61B 2018/1432* (2013.01); *A61B 2018/1475* (2013.01)

(58) Field of Classification Search
CPC .............. A61B 18/1477; A61B 18/148; A61B 2018/1432; A61B 2018/1425; A61B 2018/143; A61B 2018/1475

See application file for complete search history.

(56) References Cited

U.S. PATENT DOCUMENTS

| | | | | |
|---|---|---|---|---|
| 5,536,240 A * | 7/1996 | Edwards | ................. | A61B 18/00 604/22 |
| 5,672,173 A * | 9/1997 | Gough | ............... | A61B 18/1477 606/41 |
| 5,855,576 A * | 1/1999 | LeVeen | ............... | A61B 18/1477 606/41 |
| 6,231,570 B1 * | 5/2001 | Tu | ........................... | A61B 18/08 606/41 |
| 6,355,031 B1 * | 3/2002 | Edwards | ................. | A61B 18/12 606/102 |
| 6,974,455 B2 * | 12/2005 | Garabedian | ........ | A61B 18/1482 606/41 |
| 7,387,628 B1 * | 6/2008 | Behl | .................. | A61B 18/1477 606/41 |
| 7,416,549 B2 * | 8/2008 | Young | ................. | A61B 18/1482 606/41 |
| 2005/0065509 A1 * | 3/2005 | Coldwell | ........... | A61B 18/1477 606/41 |

* cited by examiner

*Primary Examiner* — Michael Peffley

(57) ABSTRACT

An ablation device includes a cannula having a proximal end, a distal end, and a lumen extending between the proximal and the distal ends, and a first array of electrodes at least partially disposed within the lumen, the first array of electrodes slidable relative to the cannula, each of the electrodes having a first configuration when inside the lumen, and a second configuration when unconfined outside the lumen, wherein one of the electrodes has a flared deployed profile.

18 Claims, 9 Drawing Sheets

ABLATION PROBE WITH FLARED ELECTRODES

CROSS REFERENCE TO RELATED APPLICATIONS

This application is a continuation of, and claims priority to, U.S. patent application Ser. No. 12/418,456 by Young et al. titled "Ablation probe with flared electrodes", filed Apr. 3, 2009, now U.S. Pat. No. 8,951,250, which is a continuation of U.S. patent application Ser. No. 10/977,274 by Young et al. titled "Ablation probe with flared electrodes" and filed Oct. 28, 2004, now U.S. Pat. No. 7,524,318. The entire disclosure of each of the foregoing references is incorporated herein for all purposes.

FIELD OF THE INVENTION

The field of the invention relates generally to radio frequency (RF) electrosurgical probes for the treatment of tissue, and more particularly, to electrosurgical probes having multiple tissue-penetrating electrodes that are deployed in an array to treat volumes of tissue.

BACKGROUND OF THE INVENTION

Tissue may be destroyed, ablated, or otherwise treated using thermal energy during various therapeutic procedures. Many forms of thermal energy may be imparted to tissue, such as radio frequency electrical energy, microwave electromagnetic energy, laser energy, acoustic energy, or thermal conduction. In particular, radio frequency ablation (RFA) may be used to treat patients with tissue anomalies, such as liver anomalies and many primary cancers, such as cancers of the stomach, bowel, pancreas, kidney and lung. RFA treatment involves destroying undesirable cells by generating heat through agitation caused by the application of alternating electrical current (radio frequency energy) through the tissue.

Various RF ablation devices have been suggested for this purpose. For example, U.S. Pat. No. 5,855,576 describes an ablation apparatus that includes a plurality of electrode tines deployable from a cannula. Each of the tines includes a proximal end that is coupled to a generator, and a distal end that may project from a distal end of the cannula. The tines are arranged in an array with the distal ends located generally radially and uniformly spaced apart from the distal end of the cannula. The tines may be energized in a bipolar mode (i.e., current flows between closely spaced electrode tines) or a monopolar mode (i.e., current flows between one or more electrode tines and a larger, remotely located common electrode) to heat and necrose tissue within a precisely defined volumetric region of target tissue. To assure that the target tissue is adequately treated and/or to limit damaging adjacent healthy tissues, the array of tines may be arranged uniformly, e.g., substantially evenly and symmetrically spaced-apart so that heat is generated uniformly within the desired target tissue volume.

When using the above described devices in percutaneous interventions, the cannula is generally inserted through a patient's skin, and the tines are deployed out of the distal end of the cannula to penetrate target tissue. Particularly, the tines are deployed such that the distal ends of the tines initially exit from a distal opening at the cannula. As the tines are further deployed, the distal ends of the tines evert radially away from an axis of the cannula, and then back towards a proximal end of the cannula (so that they face substantially in the proximal direction when fully deployed). As such, the tines/electrodes of the above described device each has a profile that resembles a parabola after the electrodes are deployed. The tines are then energized to ablate the target tissue.

It has been found that deployed electrodes having parabolic profiles have relatively low column strength, thereby allowing the electrodes to easily buckle. The buckling of the electrodes may occur within the cannula as the electrodes are being advanced within the cannula. In other cases, the buckling of the electrodes may occur outside the cannula as the electrodes penetrate through tissue (e.g., dense tissue). This is especially true with ablation probes that are used to create large size lesions. In such cases, longer wires are used in order to create longer tines, such that the array of tines will span across tissue have a certain size (e.g., cross-sectional area/dimension) when the tines are deployed. Since a column strength of a tine is inversely proportional to the length of the tine, creating tines using long wires will cause the tines to have low column strength. In some cases, the cross-sectional size of a tine can be increased to improve the tine's column strength. However, increasing the cross-sectional size of the tines increases the overall size of the ablation probe, making the ablation probe less desirable for treatment.

Ablation devices having a flat electrode array have been described in U.S. patent application Ser. No. 10/668,995. In such devices, the electrodes have a sharp 90° bent followed by a substantially flat/straight profile, such that the electrodes extend in directions that are substantially perpendicular to a longitudinal axis of the cannula when deployed from the cannula. Such configuration is particularly beneficial for generating flat lesions. However, in some cases, it may be desirable to generate lesions that are relatively more voluminous. Also, electrodes having the above configuration may undergo excessive bending stress (because of the sharp 90° bent) when housed within a cannula, and may be difficult to be deployed from the cannula.

Thus, there remains a need to provide for improved ablation devices having electrodes with good column strength. There is also a need to provide for improved electrodes that can be housed within a cannula without inducing excessive stress on the electrodes.

Another problem associated with existing ablation devices is that they tend to create lesions that are symmetrical. For example, another existing ablation device includes two electrode arrays that are spaced from each other, wherein the arrays have the same configuration (e.g., same deployed profile and same number of electrodes). Such ablation devices create lesions that are substantially symmetrical. However, in some cases, it may be desirable to create lesions that are asymmetric, or lesions that have other customized shapes.

SUMMARY OF THE INVENTION

In accordance with some embodiments, an ablation device includes a cannula having a proximal end, a distal end, and a lumen extending between the proximal and the distal ends, and a first array of electrodes at least partially disposed within the lumen, the first array of electrodes slidable relative to the cannula, each of the electrodes having a first configuration when inside the lumen, and a second configuration when unconfined outside the lumen, wherein a distal portion of one of the electrodes has a curvilinear body, and an angle between an axis of the cannula and an instantaneous tangent at a point along the distal portion of the body is 120° or less when the one of the electrodes is in the second configuration.

In accordance with other embodiments, a method of placing an array of electrodes within a tissue includes placing at least a portion of a cannula within a body, the cannula having a lumen, and deploying an array of electrodes having curvilinear distal portions outside the lumen such that an angle between the axis of the cannula and an instantaneous tangent at a point along the distal portion of one of the electrodes is 120° or less when the one of the electrodes is fully deployed.

In accordance with other embodiments, an ablation device includes a cannula having a proximal end, a distal end, and a lumen extending between the proximal and the distal ends, and a first array of electrodes at least partially disposed within the lumen, the first array of electrodes slidable relative to the cannula, each of the electrodes having a first configuration when inside the lumen, and a second configuration when unconfined outside the lumen, wherein one of the electrodes has a shape that resembles a half-parabola when in the second configuration.

In accordance with other embodiments, a method of placing an array of electrodes within a tissue includes placing at least a portion of a cannula within a body, the cannula having a lumen, and deploying an array of electrodes outside the lumen, wherein one of the deployed electrodes has a shape that resembles a half-parabola when the electrodes are deployed.

In accordance with other embodiments, an ablation device includes a cannula having a proximal end, a distal end, and a lumen extending between the proximal and the distal ends, and a first array of electrodes at least partially disposed within the lumen, the first array of electrodes slidable relative to the cannula, each of the electrodes having a first configuration when inside the lumen, and a second configuration when unconfined outside the lumen, wherein one of the electrodes has a flared deployed profile.

In accordance with other embodiments, a method of placing an array of electrodes within a tissue includes placing at least a portion of a cannula within a body, the cannula having a lumen, and deploying an array of electrodes outside the lumen, wherein one of the electrodes has a flared profile when in the second configuration.

In accordance with other embodiments, an ablation device includes a cannula having a distal opening, and a lumen in communication with the distal opening, and a first array of electrodes at least partially disposed within the lumen, the first array of electrodes, each of the electrodes having a first configuration when inside the lumen, and a second configuration when unconfined outside the lumen, wherein each of the electrodes has a distal tip located distal to the distal opening when the each of the electrodes is fully deployed, and a longitudinal spacing between the distal tip of one of the electrodes and the distal opening is at least 20% of the length of the one of the electrodes.

In accordance with other embodiments, a method of placing an array of electrodes within a tissue includes placing at least a portion of a cannula within a body, the cannula having a distal opening and a lumen in communication with the distal opening, and deploying an array of electrodes outside the lumen such that distal tips of the respective electrodes are distal to the distal opening, and a longitudinal spacing between the distal tip of one of the electrodes and the distal opening is at least 20% of the length of the one of the electrodes.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention. It should be noted that the figures are not drawn to scale and that elements of similar structures or functions are represented by like reference numerals throughout the figures. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
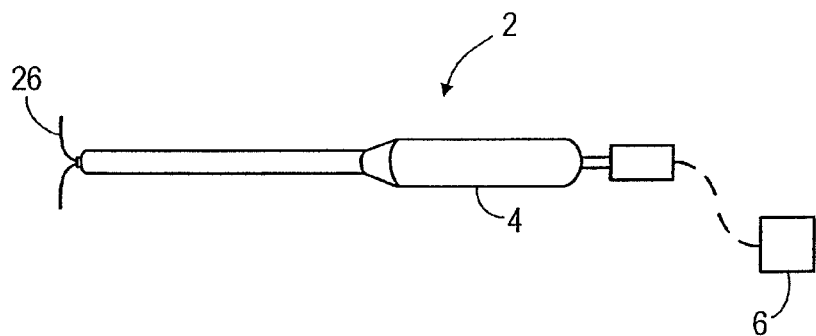
FIG. 1 is a schematic diagram of a tissue ablation system in accordance with some embodiments of the invention.

FIG. 1 illustrates a tissue ablation system 2 constructed in accordance with one embodiment of the invention. The tissue ablation system 2 generally includes a probe assembly 4 configured for introduction into the body of a patient for ablative treatment of target tissue, and a radio frequency (RF) generator 6 configured for supplying RF energy to the probe assembly 4 in a controlled manner.

Figure 2:
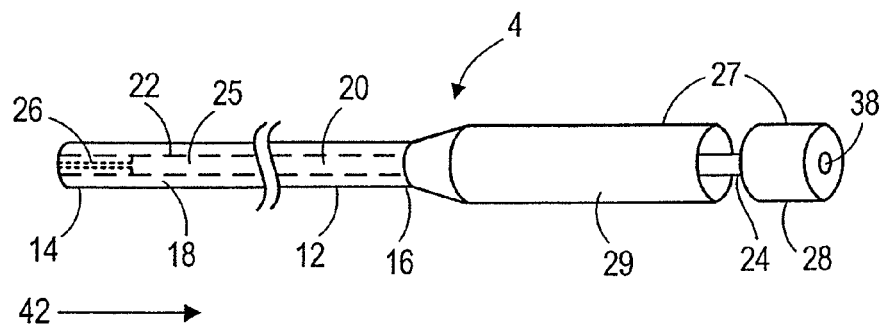
FIG. 2 is a perspective view of an ablation probe used in the system of FIG. 1, wherein an electrode array is particularly shown retracted.
Figure 3:
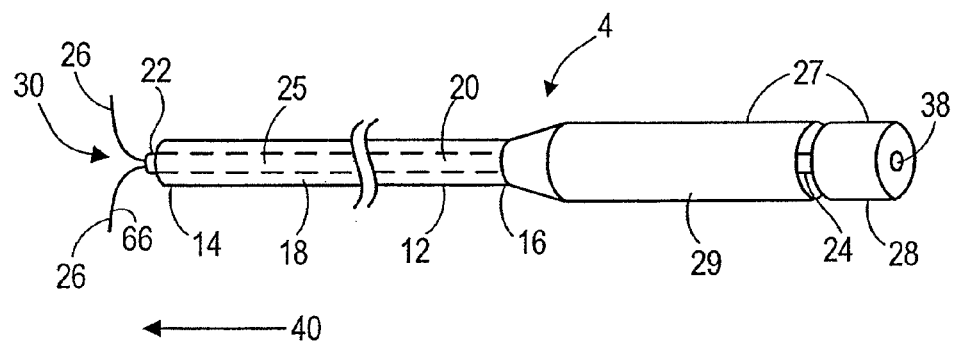
FIG. 3 is a perspective view of an ablation probe used in the system of FIG. 1, wherein an electrode array is particularly shown deployed.

Referring specifically now to FIGS. 2 and 3, the probe assembly 4 includes an elongate cannula 12, a shaft 20 slidably disposed within the cannula 12, and a plurality of electrodes 26 carried by the shaft 20. The cannula 12 has a distal end 14, a proximal end 16, and a central lumen 18 extending through the cannula 12 between the distal end 14 and the proximal end 16. The cannula 12 may be rigid, semi-rigid, or flexible depending upon the designed means for introducing the cannula 12 to the target tissue. The cannula 12 is composed of a suitable material, such as plastic, metal or the like, and has a suitable length, typically in the range from 5 cm to 30 cm, preferably from 10 cm to 20 cm. The length of the cannula 12 can also have other dimensions. If composed of an electrically conductive material, the cannula 12 is preferably covered with an insulative material. The cannula 12 has an outside cross sectional dimension consistent with its intended use, typically being from 0.5 mm to 5 mm, usually from 1.3 mm to 4 mm. The cannula 12 may have an inner cross sectional dimension in the range from 0.3 mm to 4 mm, preferably from 1 mm to 3.5 mm. The cannula 12 can also have other outside and inner cross sectional dimensions in other embodiments.

It can be appreciated that longitudinal translation of the shaft 20 relative to the cannula 12 in a distal direction 40 deploys the electrode tines 26 from the distal end 14 of the cannula 12 (FIG. 3), and longitudinal translation of the shaft 20 relative to the cannula 12 in a proximal direction 42 retracts the shaft 20 and the electrode tines 26 into the distal end 14 of the cannula 12 (FIG. 2). The shaft 20 comprises a distal end 22 and a proximal end 24. Like the cannula 12, the shaft 20 is composed of a suitable material, such as plastic, metal or the like.

In the illustrated embodiment, each electrode 26 takes the form of an electrode tine, which resembles the shape of a needle or wire. Each of the electrodes 26 is in the form of a small diameter metal element, which can penetrate into tissue as it is advanced from a target site within the target region. In some embodiments, distal ends 66 of the electrodes 26 may be honed or sharpened to facilitate their ability to penetrate tissue. The distal ends 66 of these electrodes 26 may be hardened using conventional heat treatment or other metallurgical processes. They may be partially covered with insulation, although they will be at least partially free from insulation over their distal portions.

When deployed from the cannula 12, the array 30 of electrodes 26 has a deployed configuration that defines a volume having a periphery with a radius in the range from 0.5 to 4 cm. However, in other embodiments, the maximum radius can be other values. The electrodes 26 are resilient and pre-shaped to assume a desired configuration when advanced into tissue. In the illustrated embodiment, the electrodes 26 diverge radially outwardly from the cannula 12 in a uniform pattern, i.e., with the spacing between adjacent electrodes 26 diverging in a substantially uniform and/or symmetric pattern. The profile of the electrodes 26 will be described in further details below.

It should be noted that although a total of two electrodes 26 are illustrated in FIG. 3, in other embodiments, the probe assembly 4 can have more or fewer than two electrodes 26. In exemplary embodiments, pairs of adjacent electrodes 26 can be spaced from each other in similar or identical, repeated patterns and can be symmetrically positioned about an axis of the shaft 20. It will be appreciated that a wide variety of particular patterns can be provided to uniformly cover the region to be treated. In other embodiments, the electrodes 26 may be spaced from each other in a non-uniform pattern.

The electrodes 26 can be made from a variety of electrically conductive elastic materials. Very desirable materials of construction, from a mechanical point of view, are materials which maintain their shape despite being subjected to high stress. Certain "super-elastic alloys" include nickel/titanium alloys, copper/zinc alloys, or nickel/aluminum alloys. Alloys that may be used are also described in U.S. Pat. Nos. 3,174,851, 3,351,463, and 3,753,700, the disclosures of which are hereby expressly incorporated by reference. The electrodes 26 may also be made from any of a wide variety of stainless steels. The electrodes 26 may also include the Platinum Group metals, especially platinum, rhodium, palladium, rhenium, as well as tungsten, gold, silver, tantalum, and alloys of these metals. These metals are largely biologically inert. They also have significant radiopacity to allow the electrodes 26 to be visualized in-situ, and their alloys may be tailored to accomplish an appropriate blend of flexibility and stiffness. They may be coated onto the electrodes 26 or be mixed with another material used for construction of the electrodes 26.

The electrodes 26 have generally uniform widths and rectangular cross-sections. The rectangular cross-sections make the electrodes 26 stiffer in one direction (e.g., the transverse direction) and more flexible in another direction (e.g., the radial direction). By increasing transverse stiffness, proper circumferential alignment of the electrodes 26 within the lumen 18 of the cannula 12 is enhanced. In other embodiments, the widths of the electrodes 26 may be non-uniform, and the cross-sections of the electrodes 26 may be non-rectangular. Exemplary electrodes will have a width (in the circumferential direction) in the range from 0.2 mm to 0.6 mm, preferably from 0.35 mm to 0.40 mm, and a thickness (in the radial direction) in the range from 0.05 mm to 0.3 mm, preferably from 0.1 mm to 0.2 mm.

In the illustrated embodiments, the RF current is delivered to the electrode array 30 in a monopolar fashion, which means that current will pass from the electrode array 30, which is configured to concentrate the energy flux in order to have an injurious effect on the surrounding tissue, and a dispersive electrode (not shown), which is located remotely from the electrode array 30 and has a sufficiently large area (typically 130 $cm^2$ for an adult), so that the current density is low and non-injurious to surrounding tissue. In the illustrated embodiment, the dispersive electrode may be attached externally to the patient, e.g., using a contact pad placed on the patient's flank.

Figure 4:
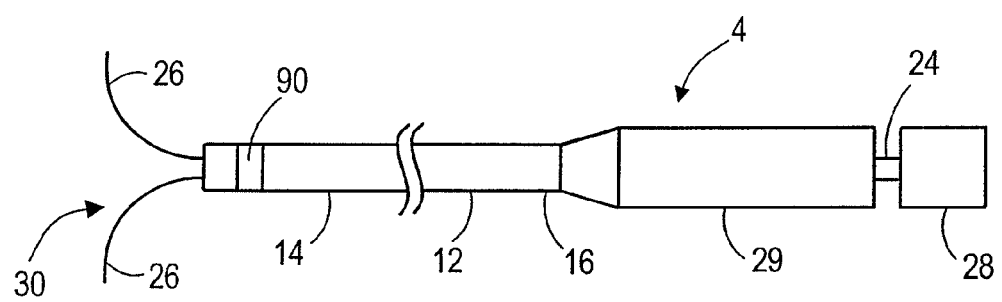
FIG. 4 is a side view of an ablation probe in accordance with other embodiments of the invention, showing the ablation probe having an electrode secured to a cannula.

Alternatively, the RF current is delivered to the electrode array 30 in a bipolar fashion, which means that current will pass between two electrodes ("positive" (or active) and "negative" (or passive/return) electrodes) of the electrode array 30, or between the electrodes of the electrode array 30 and the electrodes of another array ("positive" (or active) and "negative" (or passive/return) electrode arrays). In a bipolar arrangement, the positive and negative electrodes or electrode arrays will be insulated from each other in any regions where they would or could be in contact with each other during the power delivery phase. In other embodiments, the probe assembly 4 can further include an electrode 90 secured to the cannula 12 (FIG. 4). In such cases, the electrodes 26 in the array 30 can be active electrodes while the electrode 90 functions as return electrode for completing energy path(s). Alternatively, the electrode 90 can be active electrode while the electrodes 26 in the array 30 functions as return electrodes for completing energy path(s).

Returning to FIGS. 2 and 3, the probe assembly 4 further includes a handle assembly 27, which includes a handle portion 28 mounted to the proximal end 24 of the shaft 20, and a handle body 29 mounted to the proximal end 16 of the cannula 12. The handle portion 28 is slidably engaged with the handle body 29 (and the cannula 20). The handle portion 28 also includes an electrical connector 38, which allows the probe assembly 2 to be connected to the generator 6 during use. The electrical connector 38 is electrically coupled to the electrodes 26. As will be described in further detail below, the electrical connector 38 can be conveniently coupled to the electrodes 26 via the shaft 20 (which will be electrically conductive), although in other embodiments, the connector 38 can be coupled to the electrodes 26 via separate wires (not shown). The handle portion 28 and the handle body 29 can be composed of any suitable rigid material, such as, e.g., metal, plastic, or the like.

Optionally, a marker (not shown) may be placed on the handle portion 28 and/or on the proximal end 24 of the shaft 20 for indicating a rotational orientation or a position of the handle portion 28 relative to the shaft 20 (and the electrodes 26) during use. In some embodiments, the handle assembly 27 can have an indexing feature. For example, the proximal end 24 of the shaft 20 or the handle portion 28 can have one or more keys that mate with respective slot(s) at the interior surface of the cannula 12 or the handle body 29. Such indexing feature allows circumferential alignment of the shaft 20 (and the array 30) relative to the cannula 12. Angle indexing devices that may be used include those described in U.S. patent application Ser. No. 10/317,796, entitled "Angle Indexer For Medical Devices", the entire disclosure of which is expressly incorporated by reference herein. In other embodiments, the handle portion 28 may also include a locking mechanism (not shown) to temporarily lock against the shaft 20 to provide a more stable indexing. For example, the locking mechanism may include an axially-sliding clutch assembly that is slidable along an axis of the shaft 20 to thereby secure the handle portion 28 against the shaft 20. Other securing devices known in the art may also be used.

Referring back to FIG. 1, the RF generator 6 is electrically connected to the electrical connector 38, which may be directly or indirectly (e.g., via a conductor) electrically coupled to the electrode array 30. The RF generator 6 is a conventional RF power supply that operates at a frequency in the range from 200 KHz to 1.25 MHz, with a conventional sinusoidal or non-sinusoidal wave form. Such power supplies are available from many commercial suppliers, such as Valleylab, Aspen, and Bovie. Most general purpose electrosurgical power supplies, however, operate at higher voltages and powers than would normally be necessary or suitable for vessel occlusion. Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 20 W to 200 W, usually having a sine wave form, although other wave forms would also be acceptable. Power supplies capable of operating within these ranges are available from commercial vendors, such as Boston Scientific Corporation of San Jose, Calif., which markets these power supplies under the trademarks RF2000 (100 W) and RF3000 (200 W).

Figure 5:
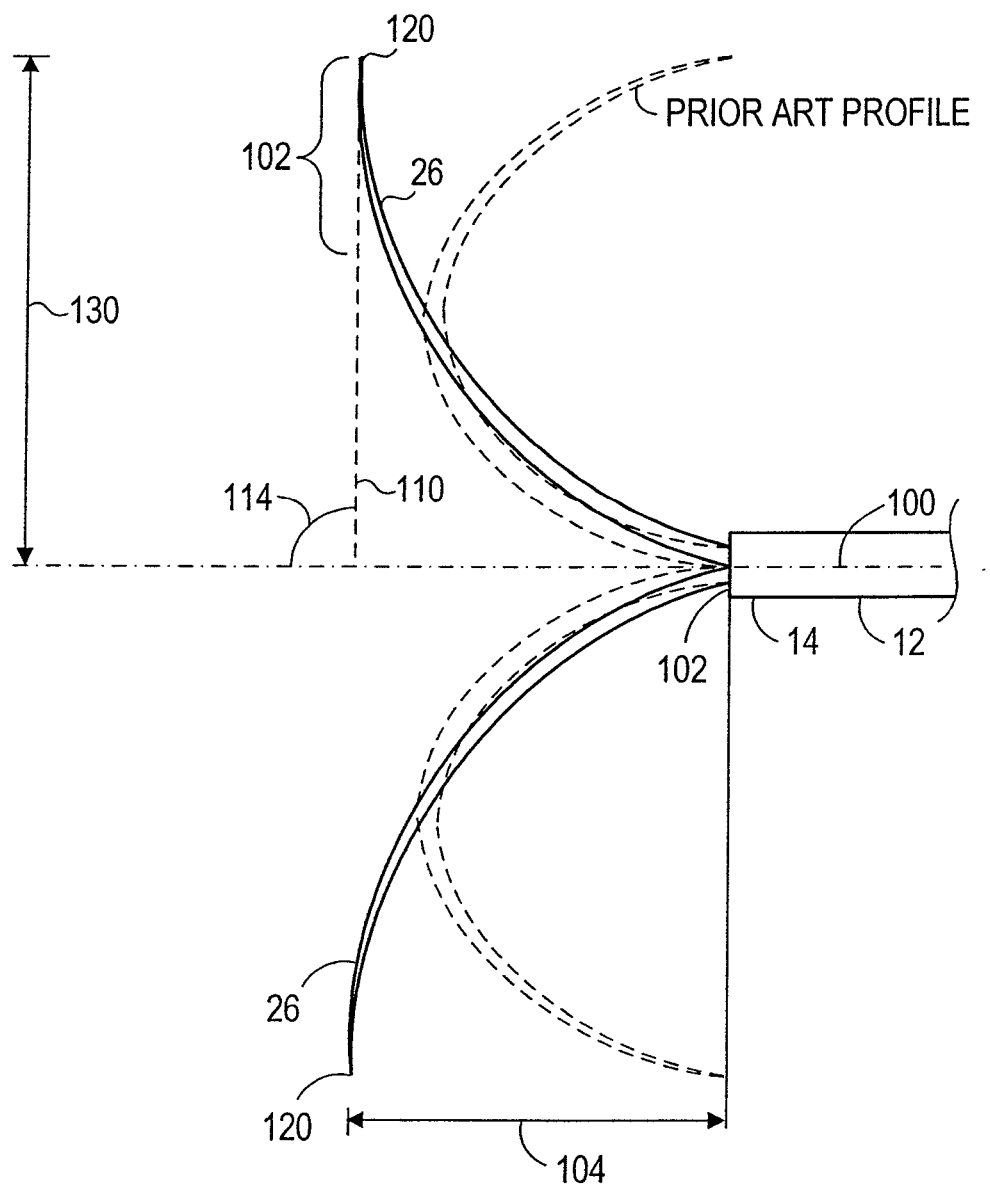
FIG. 5 is a side view of a distal end of the ablation probe of FIG. 1.

Referring now to FIG. 5, in which the profiles of the electrodes 26 are shown. In the illustrated embodiments, each electrode 26 has a flared curvilinear profile that resembles a quarter (25%) of a circular profile or elliptical profile (or a half parabola). Such configuration provides a same radius 130 of span as that for an existing electrode having a parabolic profile (shown in dotted-lines in the figure), while allowing the electrode 26 to have a shorter length than existing electrodes. As such, the electrodes 26 having the configuration shown in FIG. 5 has better column strength, and is advantageous over existing electrodes that have parabolic profiles. It should be noted that the electrodes 26 should not be limited to having flared profiles that resembles a quarter of a circular or elliptical profile, and that in alternative embodiments, the electrodes 26 can each have a flared profile that resembles other portions of a circular or elliptical profile. As used in the specification, the term "flared" is used to describe a profile of an electrode having a deployed shape that extends away from an axis, does not have a symmetric parabolic profile, and is not rectilinear along a substantial portion of its length.

Another inventive aspect of the electrodes 26 is that a distal tip 120 of each electrode 26 is longitudinally spaced at a distance 104 that is distal from an exit point 102 (the point at which the electrodes 26 exit from the cannula 12). Such configuration prevents, or at least reduce the risk of, bending of electrodes 26 as they are deployed, thereby ensuring that a deployed electrode 26 will span a radius 130 that is substantially the same as that intended. This is advantageous over existing electrodes that have symmetric parabolic profiles, in which case, a bending of an electrode may result in a deployed electrode having a span radius 130 that is smaller or larger than that originally intended. The curvilinear profile of the electrodes 26 shown in the illustrated embodiments is also advantageous over deployed electrodes that are substantially straight and extend substantially perpendicular to an axis of the cannula in that the curvilinear profile reduces stress on the electrodes 26 when the electrodes 26 are bent and confined within the cannula. The curvilinear profile also allows the electrodes 26 to exit easily from the cannula 12 as the electrodes 26 are deployed. In some embodiments, the distance 104 is equal to at least 20% of the length of an electrode 26.

In other embodiments, the profile of each electrode 26 can be characterized by the fact that an instantaneous tangent 110 at a point (e.g, a distal tip 120) along a distal portion 102 of the electrode 26 forms an angle 114 that is between 45° and 120°, and more preferably, between 80° and 100° (e.g., approximately 90°), from an axis 100 of the cannula 12. In the illustrated embodiments, the distal portion 102 includes a distal 5%, and more preferably, a distal 10%, of the length of the deployed electrode 26. In other embodiments, the distal portion 102 can include more than a distal 10% (e.g., 50%) of the length of the deployed electrode 26.

Figure 6:
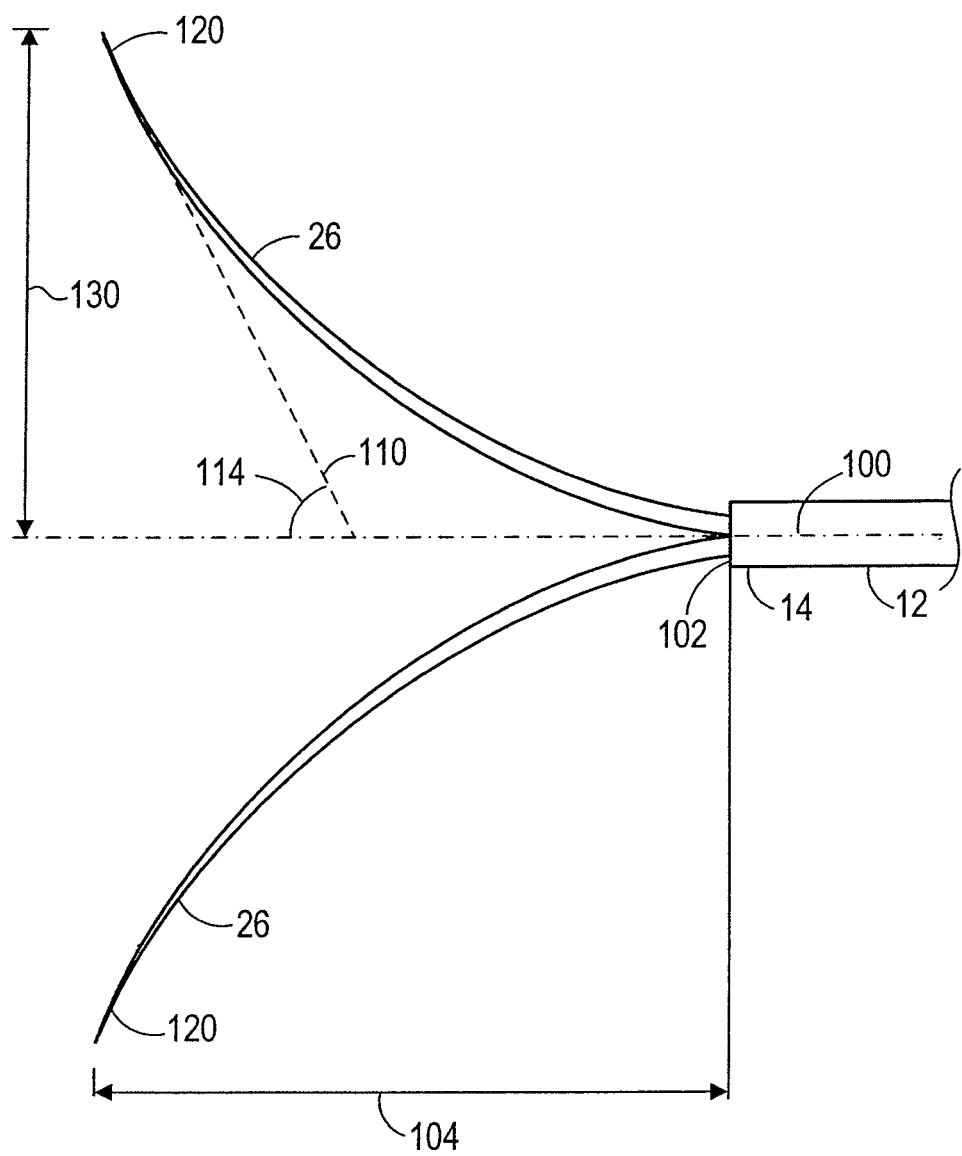
FIG. 6 is a side view of a distal end of an ablation probe in accordance with other embodiments of the invention.

It should be noted that the shape and configuration of the electrodes 26 should not be limited to that described previously, and that the electrodes 26 may have other pre-formed shapes. For example, in other embodiments, the array 30 of electrodes 26 can have a deployed configuration that resembles a cone (FIG. 6).

Figure 7A:
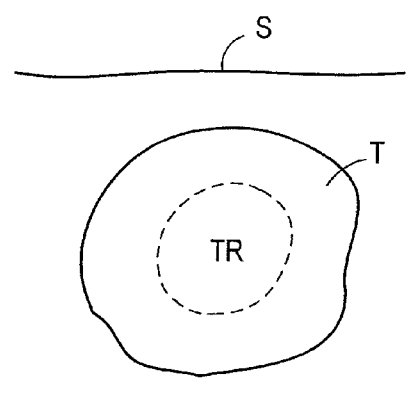
FIGS. 7A-7D are cross-sectional views, showing a method for treating tissue, in accordance with some embodiments of the invention.
Figure 7B:
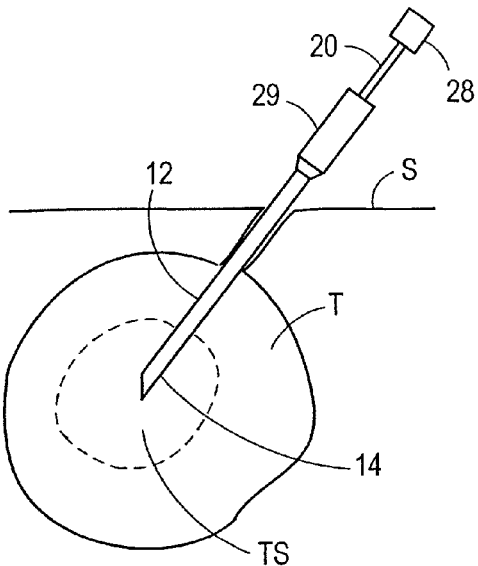

Referring now to FIGS. 7A-7D, the operation of the tissue ablation system 2 is described in treating a treatment region TR within tissue T located beneath the skin or an organ surface S of a patient. The cannula 12 is first introduced within the treatment region TR, so that the distal end 14 of the cannula 12 is located at the target site TS, as shown in FIG. 7B. This can be accomplished using any one of a variety of techniques. In some cases, the cannula 12 and shaft 20 may be introduced to the target site TS percutaneously directly through the patient's skin or through an open surgical incision. In this case, the cannula 12 may have a sharpened tip, e.g., in the form of a needle, to facilitate introduction to the target site TS. In such cases, it is desirable that the cannula 12 be sufficiently rigid, i.e., have a sufficient column strength, so that it can be accurately advanced through tissue T. In other cases, the cannula 12 may be introduced using an internal stylet that is subsequently exchanged for the shaft 20 and electrode array 30. In this latter case, the cannula 12 can be relatively flexible, since the initial column strength will be provided by the stylet. More alternatively, a component or element may be provided for introducing the cannula 12 to the target site TS. For example, a conventional sheath and sharpened obturator (stylet) assembly can be used to initially access the tissue T. The assembly can be positioned under ultrasonic or other conventional imaging, with the obturator/stylet then removed to leave an access lumen through the sheath. The cannula 12 and shaft 20 can then be introduced through the sheath lumen, so that the distal end 14 of the cannula 12 advances from the sheath to the target site TS.

Figure 7C:
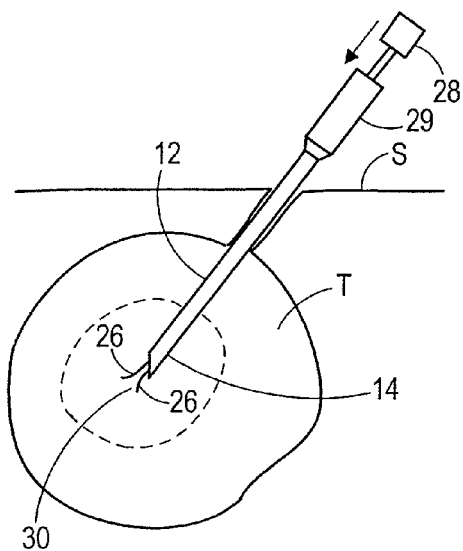
Figure 7D:
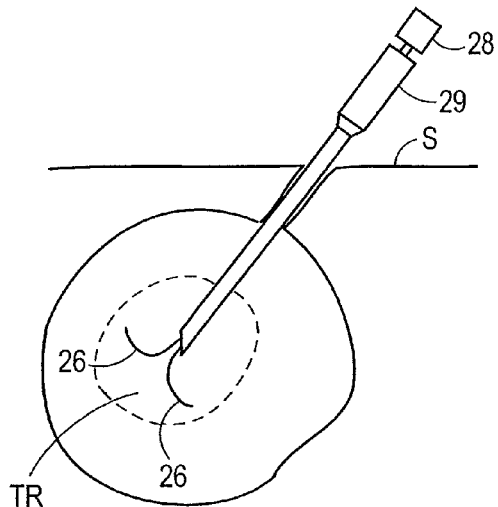

After the cannula 12 is properly placed, the shaft 20 is distally advanced to deploy the electrode array 30 radially outward from the distal end 14 of the cannula 12, as shown in FIG. 7C. The shaft 20 will be advanced sufficiently, so that the electrode array 30 is fully deployed to span at least a portion of the treatment region TR, as shown in FIG. 7D. Alternatively, the needle electrodes 26 may be only partially deployed or deployed incrementally in stages during a procedure. The inventive profile of the needle electrodes 26 prevents, or at least reduces the chance of, buckling of the electrodes 26 as the electrodes 26 are being deployed.

Next, the RF generator 6 is then connected to the probe assembly 4 (or 200) via the electrical connector 38, and the RF generator 6 is operated to deliver ablation energy to the needle electrodes 26 either in a unipolar mode or a bipolar mode. As a result, the treatment region TR is necrosed, thereby creating a lesion on the treatment region TR.

In many cases, a single ablation may be sufficient to create a desired lesion. However, if it is desired to perform further ablation to increase the lesion size or to create lesions at different site(s) within the treatment region TR or elsewhere, the needle electrodes 26 may be introduced and deployed at different target site(s), and the same steps discussed previously may be repeated. When a desired lesion at treatment region TR has been created, the needle electrodes 26 are retracted into the lumen 18 of the cannula 12, and the probe assembly 4 is removed from the treatment region TR.

Figure 8:
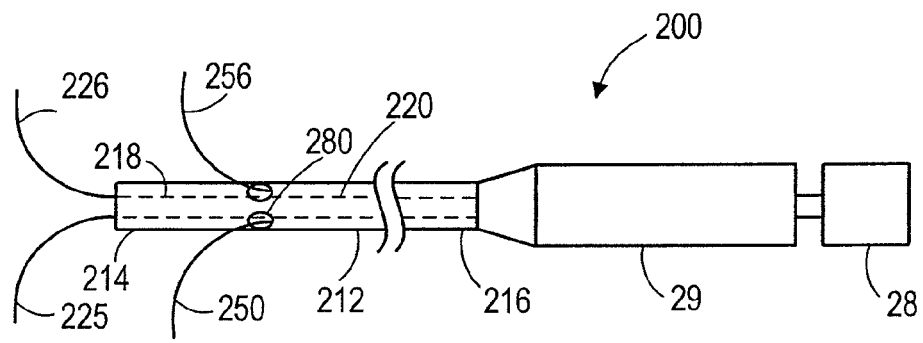
FIG. 8 is a side view of an ablation probe having two electrode arrays in accordance with other embodiments of the invention.

Although the probe assembly 4 has been described as having a single array of electrodes, in other embodiments, the probe assembly 4 can include more than one array of electrodes 26. FIG. 8 illustrates a probe assembly 200 having a plurality of arrays of electrodes in accordance with other embodiments of the invention. The probe assembly 200 includes an elongate cannula 212, a shaft 220 slidably disposed within the cannula 212, and a first array 225 of electrodes 226 carried by the shaft 220. The cannula 212 has a distal end 214, a proximal end 216, and a central lumen 218 extending through the cannula 212 between the distal end 214 and the proximal end 216. The electrodes 226 have the same profiles as the electrodes 26 described previously.

The probe assembly 200 further includes a second array 250 of electrodes 256 slidably disposed within the cannula 212. In the illustrated embodiments, the second array 250 is secured to the shaft 220. As such, distal advancement of the shaft 220 will deploy both the first and the second arrays 225, 250 of electrodes. The cannula 212 further includes openings 280 through its wall for allowing the electrodes 256 to exit from the lumen 218 when they are deployed.

The electrodes 226 in the first array 225 are active electrodes while the electrodes 256 in the second array 250 are passive/return electrodes, thereby allowing the arrays 225, 250 to be operated in a bipolar arrangement. Alternatively, the electrodes 226 in the first array 225 are passive/return electrodes while the electrodes 256 in the second array 250 are active electrodes. Also, in other embodiments, the electrodes in both arrays 226, 256 can be active electrodes. In such cases, an electrode pad can be placed on a patient's skin to complete the energy path, thereby allowing the arrays 226, 256 of electrodes to be operated in a monopolar arrangement. In further embodiments, one or more electrodes 226 in the first array 225 can be active electrode(s) that operate in a bipolar arrangement with another electrode 226 (serving as a return electrode) in the first array 225. Similarly, one or more electrodes 256 in the second array 250 can be active electrode(s) that operate in a bipolar arrangement with another electrode 256 (serving as a return electrode) in the second array 250. In some embodiments, one or more of the electrodes in the first and the second arrays 226, 256 can have portion(s) that is electrically insulated to achieve desired energy path(s).

Figure 9:
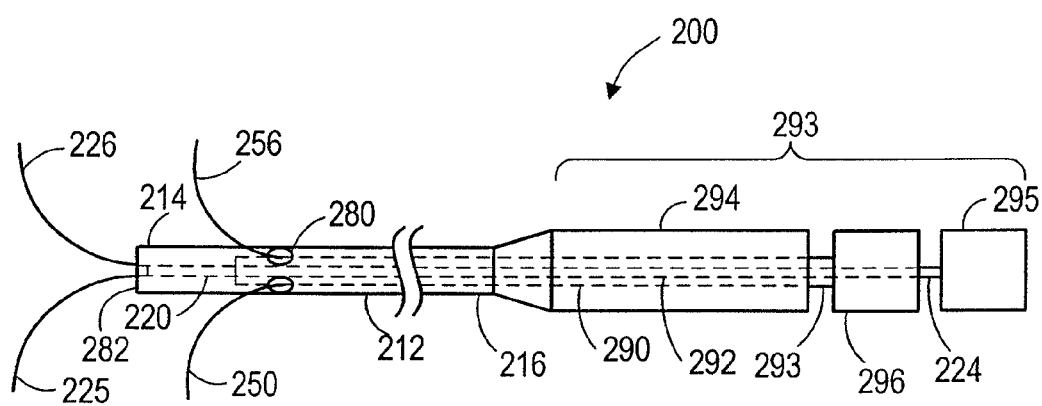
FIG. 9 is a side view of an ablation probe having two electrode arrays in accordance with other embodiments of the invention, showing the arrays being deployed by separate shafts.

In other embodiments, instead of securing the second array 250 to the same shaft 220, the second array 250 is secured to another shaft 290 having a lumen 292 (FIG. 9). In such cases, the first shaft 220 is disposed within the lumen 292 of the second shaft 290. The second array 250 of electrodes can be deployed through the openings 280, or alternatively, if the cannula 212 does not have the openings 280, through the distal opening 282 at the distal end 214 of the cannula 212. The first array 225 of electrodes 226 can be deployed by advancing the shaft 220 distally relative to the cannula 212 until the electrodes 226 are unconfined outside the lumen 218 of the cannula 212, and the second array 250 of electrodes 256 can be deployed by advancing the shaft 290 distally relative to the cannula 212 until the electrodes 256 are unconfined outside the lumen 218 of the cannula 212. In the illustrated embodiments, the probe assembly 200 includes a handle assembly 293 having a handle body 294, a first handle portion 295 secured to a proximal end 224 of the first shaft 220, and a second handle portion 296 secured to a proximal end 293 of the second shaft 290. The first handle portion 295 and the second handle portion 296 can be positioned relative to the handle body 294 for deploying the first and the second arrays 225, 250, respectively.

Figure 10:
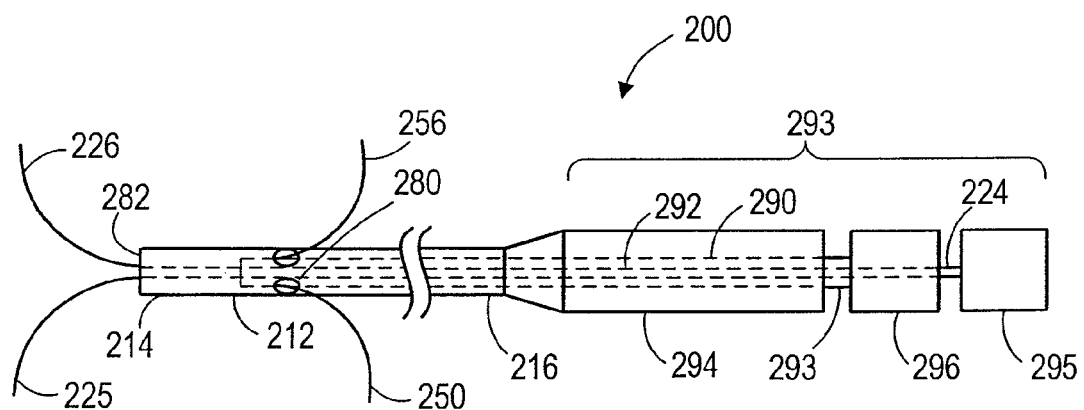
FIG. 10 is a side view of an ablation probe in accordance with other embodiments of the invention, showing the ablation probe having two arrays of electrodes facing in opposite directions.

In the illustrated embodiments, the electrodes 256 in the second array 250 have profiles that are the same or similar to those of the electrodes 226 in the first array 225, and the two arrays 225, 250 face towards the same direction. In other embodiments, instead of having the two arrays 225, 250 of electrodes facing towards the same direction, the two arrays of electrodes can face towards each other in opposite directions (FIG. 10). In such cases, the second array 250 of electrodes 256 are deployed out of the openings 280 by retracting the second handle portion 296 proximally relative to the handle body 294, and the first array 225 of electrodes 226 are deployed out of the distal opening 282 by advancing the first handle portion 295 distally relative to the handle body 294.

It should be noted that although a total of two electrodes are illustrated for each of the arrays 225, 250 in FIGS. 8-10, in other embodiments, the probe assembly 200 can have more or fewer than two electrodes per array.

Figure 11:
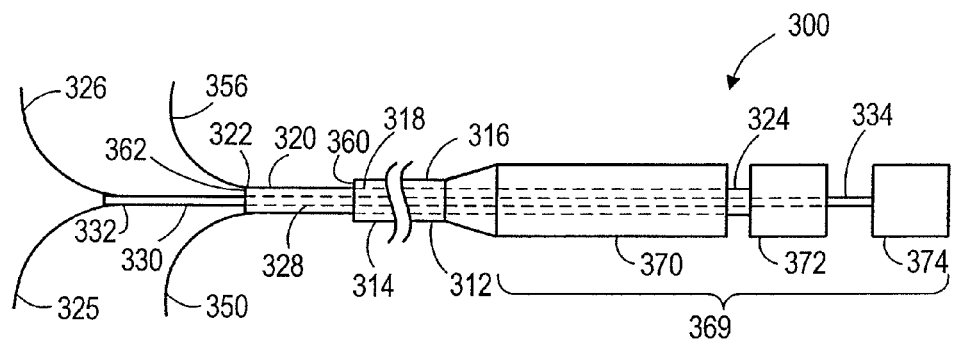
FIG. 11 is a side view of an ablation probe in accordance with other embodiments of the invention, showing the ablation probe having two arrays of electrodes that are slidable relative to each other.

In the above embodiments, the electrodes 256 are deployed out of the cannula 212 via the openings 280. Alternatively, the electrodes 256 can be deployed through the distal opening 282 of the cannula 212. FIG. 11 illustrates an ablation probe 300 in accordance with other embodiments of the invention. The probe assembly 300 includes an elongate cannula 312, a first shaft 330, a first array 325 of electrodes 326 secured to a distal end 332 of the first shaft 330, a second shaft 320, and a second array 350 of electrodes 356 secured to a distal end 322 of the second shaft 320. The cannula 312 has a distal end 314, a proximal end 316, and a central lumen 318 extending through the cannula 312 between the distal end 314 and the proximal end 316. The electrodes 326, 356 have the same profiles as the electrodes 26 described previously.

In the illustrated embodiments, the first shaft 330 is slidably disposed within a lumen 328 of the second shaft 320, and the second shaft 320 is slidably disposed within the lumen 318 of the cannula 312. The second array 350 can be deployed by advancing the second shaft 320 distally relative to the cannula 312 (or retracting the cannula 312 proximally relative to the second shaft 320) until the second array 350 of electrodes 356 exit from a distal opening 360 at the distal end 314 of the cannula. The first array 325 can be deployed by advancing the first shaft 330 distally relative to the second shaft 320 (or retracting the second shaft 320 proximally relative to the first shaft 330) until the first array 325 of electrodes 326 exit from a distal opening 362 at the distal end 322 of the second shaft 320. Such configuration is beneficial because it allows a distance between the first and the second arrays to be adjusted during use. It should be noted that the probe assembly 300 should not be limited to electrodes having the illustrated deployed profiles, and that in other embodiments, one or both of the arrays 325, 350 can have electrodes with other deployed profiles. For example, an electrode in the first array 325 (and/or an electrode in the second array 350) can have a parabolic profile, a rectilinear profile, or a customized profile in other embodiments.

Figure 12:
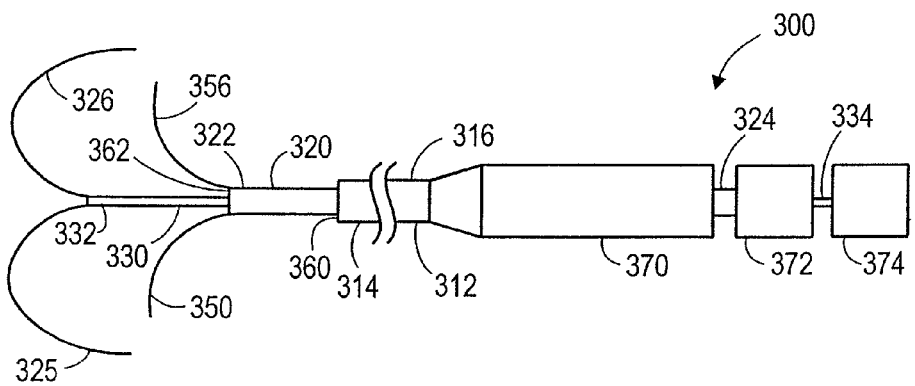
FIG. 12 is a side view of an ablation probe in accordance with other embodiments of the invention, showing the ablation probe having two electrode arrays with different configurations.
Figure 13:
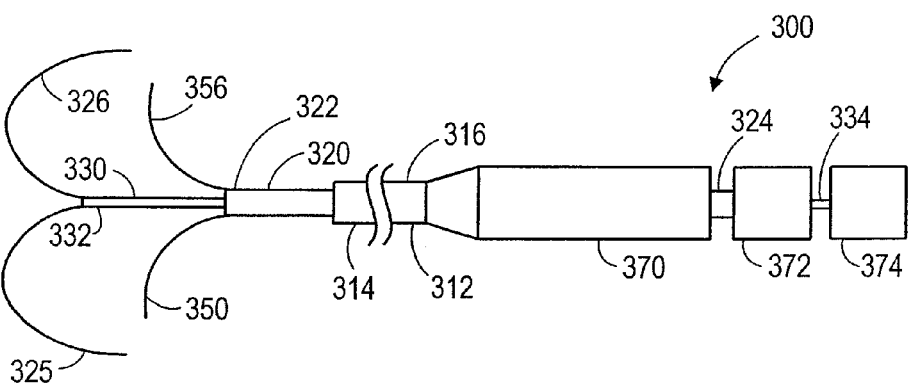
FIG. 13 is a side view of an ablation probe in accordance with other embodiments of the invention, showing the ablation probe having two electrode arrays with different configurations.

In the above embodiments, electrodes in the first and the second arrays have the same deployed profiles. In other embodiments, electrodes in the first array can have deployed profiles that are different from electrodes in the second array. Such feature is advantageous in that it allows lesions having asymmetric profile to be created. For example, in some embodiments, the electrodes 326 in the first array 325 each has a deployed profile that resembles a parabola, while the electrodes 356 in the second array 350 each has a flared deployed profile that is similar to that shown in FIG. 5 (FIG. 12). Alternatively, the electrodes 326 in the first array 325 can each have a flared deployed profile that is similar to that shown in FIG. 5, while the electrodes 356 in the second array 350 each has a parabolic deployed profile. In other embodiments, the electrodes 326 in the first array 325 each has a deployed profile that resembles a parabola, while the electrodes 356 in the second array 350 each has a flared deployed profile that is similar to that shown in FIG. 6 (with the deployed array 356 having a configuration that resembles a cone) (FIG. 13). Alternatively, the electrodes 326 in the first array 325 can each have a flared deployed profile that is similar to that shown in FIG. 6, while the electrodes 356 in the second array 350 each has a parabolic deployed profile. It should be noted that although a total of two electrodes are illustrated for each of the arrays 325, 350 in FIGS. 11-13, in other embodiments, the probe assembly 300 can have more or fewer than two electrodes per array.

Figure 14A:
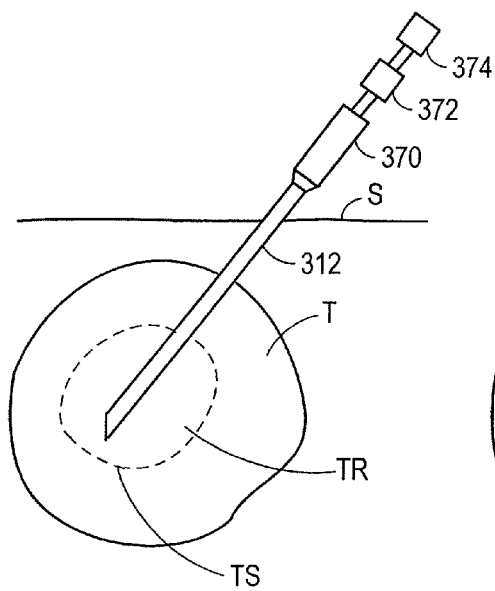
FIGS. 14A-14D are cross-sectional views, showing a method for treating tissue, in accordance with some embodiments of the invention.

It should be noted that the profiles of the deployed electrodes in the first and the second arrays 325, 350 should not be limited by the examples illustrated previously, and that the electrodes in the first and the second arrays 325, 350 can have other deployed profiles. For examples, in other embodiments, the electrodes in the first array 325 (and/or the second array 350) can each have a straight or rectilinear deployed profile, a parabolic deployed profile, the flared deployed profile shown in FIG. 5, or the flared profile shown in FIG. 6, or a deployed profile having a customized shape. Also, in other embodiments, instead of having the first and the second arrays 325, 350 facing the same direction, the first and the second arrays 325, 350 can face in the opposite directions and towards each other. In addition, although the above embodiments have been described as having the same number of electrodes per array, in any of the embodiments described herein, the first array 325 (or 225) and the second array 350 (or 250) can have different number of electrodes. Further, in other embodiments, the first array 325 can have a radius (e.g., radius 130) of span that is different from a radius of span of the second array 350. In such cases, the first and the second arrays 325, 350 can have deployed shapes that are the same or different. For example, in some embodiments, the second array 350 has a radius of span that is greater than a radius of span of the first array 325, thereby allowing the arrays 325, 350 to create a lesion having a proximal end that is larger than a distal end. Alternatively, in other embodiments, the second array 350 has a radius of span that is less than a radius of span of the first array 325, thereby allowing the arrays 325, 350 to create a lesion having a proximal end that is smaller than a distal end Referring now to FIGS. 14A-14D, the operation of the tissue ablation probe 300 is described in treating a treatment region TR within tissue T located beneath the skin or an organ surface S of a patient. The cannula 312 is first introduced within the treatment region TR, so that the distal end 314 of the cannula 312 is located at the target site TS, as shown in FIG. 14A. This can be accomplished using any one of a variety of techniques. In some cases, the cannula 312 and shafts 320, 330 may be introduced to the target site TS percutaneously directly through the patient's skin or through an open surgical incision. In this case, the cannula 312 may have a sharpened tip, e.g., in the form of a needle, to facilitate introduction to the target site TS. In such cases, it is desirable that the cannula 312 be sufficiently rigid, i.e., have a sufficient column strength, so that it can be accurately advanced through tissue T. In other cases, the cannula 312 may be introduced using an internal stylet that is subsequently exchanged for the shafts 320, 330 and electrode arrays 325, 350. In this latter case, the cannula 312 can be relatively flexible, since the initial column strength will be provided by the stylet. More alternatively, a component or element may be provided for introducing the cannula 312 to the target site TS. For example, a conventional sheath and sharpened obturator (stylet) assembly can be used to initially access the tissue T. The assembly can be positioned under ultrasonic or other conventional imaging, with the obturator/stylet then removed to leave an access lumen through the sheath. The cannula 312 and shafts 320, 330 can then be introduced through the sheath lumen, so that the distal end 314 of the cannula 312 advances from the sheath to the target site TS.

Figure 14B:
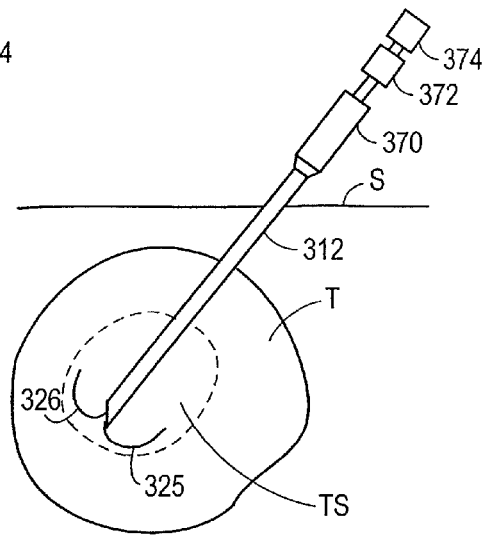

After the cannula 312 is properly placed, the first shaft 330 is distally advanced to deploy the first electrode array 325 radially outward from the distal end 314 of the cannula 312, as shown in FIG. 14B. The shaft 330 will be advanced sufficiently, so that the first electrode array 325 is fully deployed to span at least a portion of the treatment region TR. Alternatively, the needle electrodes 326 may be only partially deployed or deployed incrementally in stages during a procedure.

Figure 14C:
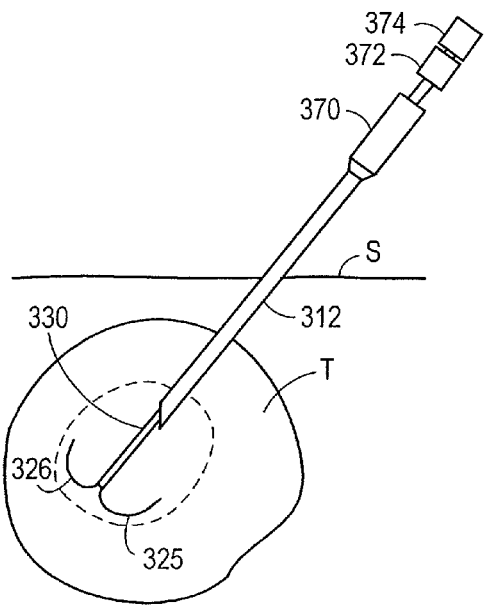
Figure 14D:
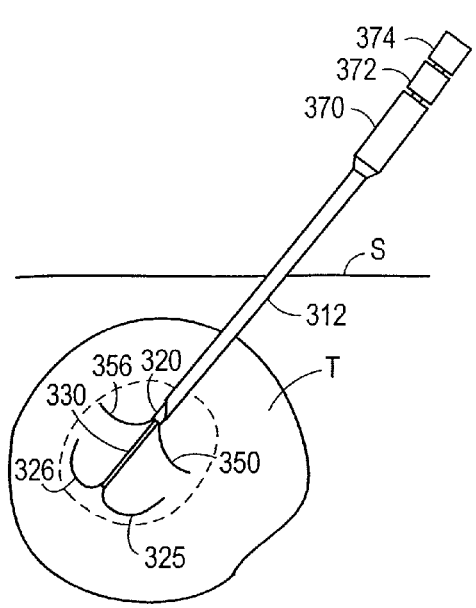

After the electrodes 326 of the first array 325 have been deployed, the cannula 312, together with the second shaft 320 are then retracted proximally until the distal end 314 of the cannula 312 is desirably positioned (FIG. 14C). The electrodes 356 of the second array 350 are then advanced distally (e.g., by advancing the second handle portion 372 distally relative to the handle body 370) until they exit from the lumen 318 of the cannula 312, thereby deploying the second array 350 of electrodes 356 (FIG. 14D).

In alternative embodiments, instead of deploying the first array 325 before the second array 350, the second array 350 can be deployed before the first array 325. In such cases, the second array 350 can be deployed by advancing the second handle portion 372 distally relative to the handle body 370. After the second array 350 has been deployed, the first array 325, being confined within a sheath (not shown), is then advanced distally together with the sheath until the distal end of the sheath exits from the lumen 328 of the second shaft 320 and is desirably positioned. The sheath is then retracted proximally to deploy the first array 325 of electrodes 326.

Next, the RF generator 6 is then connected to the probe assembly 300, and the RF generator 6 is operated to deliver ablation energy to the needle electrodes 326, 356 either in a unipolar mode or a bipolar mode. As a result, the treatment region TR is necrosed, thereby creating a lesion on the treatment region TR. As a result of using arrays with different configurations, the created lesion will have an asymmetric shape.

In many cases, a single ablation may be sufficient to create a desired lesion. However, if it is desired to perform further ablation to increase the lesion size or to create lesions at different site(s) within the treatment region TR or elsewhere, the needle electrodes 326, 356 may be introduced and deployed at different target site(s), and the same steps discussed previously may be repeated. When a desired lesion at treatment region TR has been created, the needle electrodes 326 are retracted into the lumen 328 of the second shaft 320, and the electrodes 356 (together with the retracted electrodes 326) are retracted into the lumen 318 of the cannula 312. The probe assembly 300 is then removed from the treatment region TR.

Although the method has been described with reference to the ablation probe 300, the same or similar method can be used with other embodiments of ablation probe assembly described herein.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. For example, the array (e.g., array 30, 225, 250, 325, or 350) of electrodes can be manufactured as a single component. As such, the "array of electrodes" should not be limited to a plurality of separate electrodes, and includes a single structure (e.g., an electrode) having different conductive portions. Thus, the present invention is intended to cover alternatives, modifications, and equivalents that may fall within the spirit and scope of the present invention as defined by the claims.

What is claimed:

1. An ablation device, comprising:
   a cannula having a first lumen extending within the cannula and terminating in a first opening at the distal tip of the cannula;
   a first array of electrodes secured to a first shaft having a second lumen extending within the first shaft and terminating in a second opening at the distal tip of the first shaft, said first array of electrodes having a rectangular cross-section and being deployable from within the first lumen, wherein each of the electrodes in the first array of electrodes, when deployed, includes a curved proximal portion and a substantially straight distal portion, the substantially straight distal portion extending perpendicular to a long axis of the cannula; and
   a second array of electrodes secured to a second shaft and deployable from within the second lumen, said second array of electrodes being slidable relative to the first array of electrodes.

2. The ablation device of claim 1, wherein the number of electrodes in the first array is different from the number of electrodes in the second array.

3. The ablation device of claim 1, wherein the first and the second arrays face the same way.

4. The ablation device of claim 1, wherein the first and the second arrays face opposite one another.

5. The ablation device of claim 1, wherein the first array of electrodes has a deployed shape that is different from a deployed shape of the second array of electrodes.

6. The ablation device of claim 5, wherein the first array has a first radius of span, wherein the second array has a second radius of span, and wherein the second radius of span is different from the first radius of span.

7. The ablation device of claim 6, wherein each of the electrodes in the second array of electrodes has a deployed profile that resembles a parabola.

8. The ablation device of claim 5, wherein the first array has a first radius of span, wherein the second array has a second radius of span, and wherein the second radius of span is greater than the first radius of span.

9. An ablation device, comprising:
   a cannula having a distal tip and a first lumen extending within the cannula and terminating in an opening at the distal tip;
   a first array of electrodes secured to a first shaft having a second lumen, said first array of electrodes having a rectangular cross-section and being disposed within the first lumen and deployable from the distal tip opening, each of the electrodes in the first array of electrodes having a first configuration when inside the lumen and a second configuration when fully deployed outside the lumen and having an angle between an axis of the cannula and an instantaneous tangent at a point along a distal portion of the electrode that is between 80° and 100° when in the second configuration; and
   a second array of electrodes secured to a second shaft and deployable from within the second lumen, said second array of electrodes being slidable relative to the first array of electrodes.

10. The ablation device of claim 9, wherein a longitudinal spacing between a distal tip of the at least one electrode in the first array and the distal tip opening of the cannula is at least 20% of the length of the at least one electrode in the first array.

11. The ablation device of claim 9, wherein the number of electrodes in the first array is different from the number of electrodes in the second array.

12. The ablation device of claim 9, wherein each of the electrodes in the first and the second arrays face the same way.

13. The ablation device of claim 9, wherein each of the electrodes in the first and the second arrays face opposite one another.

14. The ablation device of claim 9, wherein each of the at least one electrode in the first array of electrodes has a deployed shape that is different from a deployed shape of the at least one electrode in the second array of electrodes.

15. The ablation device of claim 14, wherein the first array has a first radius of span, wherein the second array has a second radius of span, and wherein the second radius of span is different from the first radius of span.

16. The ablation device of claim 15, wherein each of the electrodes in the second array of electrodes has a deployed profile that resembles a parabola.

17. The ablation device of claim 14, wherein the first array has a first radius of span, wherein the second array has a second radius of span, and wherein the second radius of span is greater than the first radius of span.

18. A method of treating a patient, comprising the steps of:
placing at least a portion of a cannula within a body, the cannula having a first lumen that terminates in an first opening in a distal tip thereof;
deploying from the first lumen a first array of electrodes secured to a first shaft having a second lumen extending within the first shaft and terminating in a second opening at the distal tip of the first shaft, said first array of electrodes having a rectangular cross-section from the distal tip opening, each of the electrodes having a deployed configuration that includes a curved proximal portion and a substantially straight distal portion, the substantially straight portion extending perpendicular to a long axis of the cannula;
deploying from the second lumen a second array of electrodes secured to a second shaft, said second array of electrodes being slidable relative to the first array of electrodes; and
energizing the first and second arrays of electrodes, thereby ablating a target tissue in the patient.

* * * * *